United States Patent [19]

Thomson et al.

[11] 4,404,396
[45] Sep. 13, 1983

[54] PROCESS FOR THE PREPARATION OF 2-(2,4-DICHLOROPHENOXY)-PHENYLACETIC ACID

[75] Inventors: Colin Thomson, Loughborough; Neil J. Tweddle, Thorngumbald, both of England

[73] Assignee: Reckitt & Colman Products Limited, London, England

[21] Appl. No.: 338,492

[22] Filed: Jan. 11, 1982

[30] Foreign Application Priority Data

Jan. 24, 1981 [GB] United Kingdom ................. 8102197

[51] Int. Cl.³ .......................................... C07C 65/00
[52] U.S. Cl. ..................................... 562/465; 560/55; 560/62
[58] Field of Search ..................... 562/465; 560/55, 62

[56] References Cited

U.S. PATENT DOCUMENTS 4,128,573 12/1978 Adams et al. ........................ 562/465

FOREIGN PATENT DOCUMENTS 17882 10/1980 European Pat. Off ............. 562/465
1308327 2/1973 United Kingdom ................ 562/465

*Primary Examiner*—Paul J. Killos
*Attorney, Agent, or Firm*—Bacon & Thomas

[57] ABSTRACT

Process for the preparation of 2-(2,4-dichlorophenoxy)-phenylacetic acid in which the potassium salts of 2-chlorophenylacetic acid and 2,4-dichlorophenol are reacted in aromatic hydrocarbon solvents at elevated temperatures in the presence of a copper chloride catalyst, followed thereafter by acidification.

4 Claims, No Drawings

PROCESS FOR THE PREPARATION OF 2-(2,4-DICHLOROPHENOXY)-PHENYLACETIC ACID

This invention relates to an improved process for the preparation of an arylalkanoic acid and in particular to an improved process for the preparation of 2-(2,4-dichlorophenoxy)phenylacetic acid.

2-(2,4-Dichlorophenoxy)phenylacetic acid (fenclofenac) has been shown in clinical trials in man to be a valuable anti-inflammatory drug with minimal gastric side effects.

Hitherto this compound has been prepared by reacting o-chloroacetophenone with the sodium or potassium salt of 2,4-dichlorophenol at a temperature of at least 120° C. in the presence of a copper catalyst to produce 2-(2,4-dichlorophenoxy)acetophenone. This is then reacted with sulphur and morpholine to afford a thioacetmorpholide which is thereafter hydrolysed.

This overall process suffers from a number of disadvantages, including the use of expensive raw materials, a first stage involving a long reaction time (24 hours), the overall yield of the processes being low. A further disadvantage when the process is to be scaled up to a tonnage level is that o-chloroacetophenone is not commercially available in the required quantities and has therefore itself to be manufactured on a large scale. Unfortunately its manufacture involves a Grignard reaction which because of the hazardous nature of the reaction can only be carried out on a limited batch scale, and therefore for the quantities of material required considerable duplication of equipment is necessary.

It has now been found possible to develop an alternative process for the preparation of 2-(2,4-dichlorophenoxy)phenylacetic acid which is capable of scaling up to yield tonnage quantities.

According to this invention there is provided a process for the preparation of 2-(2,4-dichlorophenoxy)-phenylacetic acid in which equimolar proportions of the potassium salts of 2-chlorophenylacetic acid and 2,4-dichlorophenol are reacted in toluene, xylene, ethylbenzene, cumene, or mixtures thereof, at a temperature in the range 100° C. to the boiling point of the reaction mixture, in the presence of a copper chloride catalyst, followed thereafter by acidification.

Conveniently the reaction is carried out at reflux. The xylene employed may be ortho-, meta-, or para-xylene or mixtures thereof.

The copper chloride catalyst may be cupric chloride, cuprous chloride or cuprous chloride/triphenylphosphine complex, a preferred complex being the mono triphenylphosphine complex. The catalyst is conveniently used at a molar ratio of 0.02 to 0.10 based on the potassium salts.

A particularly convenient method of carrying out the process is to dissolve equimolar proportions of 2-chlorophenylacetic acid and 2,4-dichlorophenol in the reaction solvent (e.g. xylene), to add 2 molar equivalents of potassium hydroxide (as a concentrated aqueous solution or solid caustic potash plus a small amount of water) and heat the mixture to azeotropically remove the water, with the copper chloride catalyst being added before or after the azeotropic removal of the water. Optimum yields of the desired product occur after about 5 hours reaction.

During the reaction a precipitate comprising a mixture of potassium chloride and the potassium salt of fenclofenac is formed. The reaction mixture may be conveniently worked up according to one of two procedures, (a) by filtering off the precipitated salts, washing with a further amount of the reaction solvent (e.g. xylene) or tetrachloroethylene, drying to remove traces of the solvent, dissolving in water and precipitating the fenclofenac by the addition of acid (e.g. conc hydrochloric acid), or (b) extracting the mixture with water, washing the aqueous extracts with a further amount of the reaction solvent (e.g. xylene) or tetrachloroethylene (to remove neutral impurities) and precipitating the fenclofenac by the addition of acid (e.g. conc hydrochloric acid). The resultant fenclofenac obtained by either of these procedures may be further purified by recrystallisation from e.g. tetrachloroethylene.

It has been found that the substitution of sodium salts for the potassium salts in the process of the present invention leads to a much slower reaction and resultant reduced yields.

The invention is illustrated by the following Examples in which temperatures are quoted in degrees Celsius.

EXAMPLE 1

Potassium hydroxide (12.44 g; 85.4% pure; 0.19 mol) in water (10 mls) was added to 2-chlorophenylacetic acid (17.05 g; 0.1 mol) and 2,4-dichlorophenol (16.3 g; 0.1 mol) in xylene (100 ml; isomer mixture, sulphur free), with additional water (5 ml) being used to wash in any remaining potassium hydroxide solution. The mixture was heated with stirring under nitrogen and the azeotroped water collected using a Dean and Stark apparatus. After 4 hours water (19 ml) and xylene (31 ml) had been removed. Heating was discontinued, additional xylene (31 ml) was added and the mixture was sealed and allowed to stand overnight at room temperature.

The mixture was reheated to 100° under nitrogen to melt the solids. Cupric chloride anhydrous (0.27 g; 0.002 mol) was added with stirring and the mixture heated at reflux. The course of the reaction was monitored with samples being analysed by h.p.l.c. Heating was discontinued after 5¾ hours when the mixture was allowed to cool to below 100° when the mixture became almost solid. Water (50 ml) was added and the mixture stirred until all the solid had dissolved. The aqueous layer was separated, the xylene layer was extracted with water (50 ml) and the combined aqueous extracts washed with tetrachloroethylene (10 ml). The aqueous extracts were acidified to pH 4 by the addition of conc. hydrochloric acid. The precipitated product, an oil which solidified on scratching, was collected, washed with water and dried in vacuo (60°) to afford 2-(2,4-dichlorophenoxy)phenylacetic acid as an off-white solid (25.8 g; 87% yield). The solid was recrystallised from tetrachloroethylene (20 ml), the product being collected, washed with tetrachloroethylene (2×5 ml) and dried in vacuo (60°) to afford pure product (19.6 g; 67% yield) m.p. 135°–136°.

EXAMPLE 2

The procedure of Example 1 was repeated using cuprous chloride (0.2 g; 0.002 mol) as catalyst in place of cupric chloride, the reaction mixture being heated at reflux (temperature 137°) for 3½ hours. The yield of crude product was 25.2 g (85% yield) and the yield after recrystallisation was 19.5 g (66% yield).

EXAMPLE 3

Potassium hydroxide (24.88 g; 85.4% pure; 0.38 mol) in water (20 ml) was added to 2-chlorophenylacetic acid (34.1 g; 0.2 mol) and 2,4-dichlorophenol (32.6; g; 0.2 mol) in xylene (100 ml) with additional water (10 ml) being used to wash in the potassium hydroxide solution. The mixture was stirred until all solids had dissolved. Cuprous chloride 0.4 g; 0.004 mol) was then added and the mixture heated under nitrogen and the azeotroped water collected using a Dean and Stark apparatus. After 2 hours all the water had been removed (40 ml), the reflux temperature reaching 136°. Heating was continued for a further 4 hours and then the mixture was cooled to room temperature and allowed to stand overnight. Water (100 ml) was added amd the aqueous layer was separated.

The xylene layer was extracted with water (100 ml) and the combined aqueous extracts were washed with tetrachloroethylene (2×20 ml). The aqueous extracts were acidified with conc. hydrochloric acid (13 ml). The product was obtained as in Example 1 after drying as a pinkish solid (47.9 g; 81% yield).

The solid (35.0 g) was recrystallised from tetrachloroethylene (35 ml), the product being collected, washed with tetrachloroethylene (2×10 ml) and dried in vacuo (60°) to afford a very pale pink solid (27.1 g; 62% yield).

EXAMPLE 4

A mixture of potassium hydroxide (39.9 g), water (1 ml), 2-chlorophenylacetic acid (53.2 g) and 2,4-dichlorophenol (50.9 g) in xylene (150 ml) was stirred under nitrogen for 1 hour and then heated to reflux and water azeotroped off over 4 hours. Additional xylene to replace xylene that had been collected was added followed by the addition of cuprous chloride (1.54 g) and refluxing was maintained for a further 5¼ hours. The mixture was cooled to room temperature whilst adding water (150 ml), stirred for a further ½ hour and allowed to stand overnight. The aqueous layer was separated, the xylene layer was extracted with water (50 ml), and the combined aqueous extracts filtered and washed with xylene (3×50 ml). The aqueous extracts were acidified with conc. hydrochloric acid (23 ml), xylene (70 ml) was added and the mixture heated to 90° and stirred at 90° for 1½ hours and then cooled overnight to room temperature (20°). The solid product was filtered off, resuspended in a mixture of water (50 ml) and tetrachloroethylene (50 ml) and re-filtered, and sucked as dry as possible. A sample of the damp solid (109.4 g) was dried to give an estimated dry yield of 62 g (67% yield).

EXAMPLE 5

Following the procedure of Example 1 a mixture of potassium hydroxide (12.44 g; 0.19 mol), water (15 ml), 2-chlorophenylacetic acid (17.05 g; 0.1 mol) and 2,4-dichlorophenol (16.3 g; 0.1 mol) in xylene (200 ml) was heated to remove the water azeotropically, additional xylene (38 ml) was added, and the mixture sealed and allowed to stand overnight.

The mixture was heated to 125° under nitrogen and cuprous chloride/monotriphenylphosphine complex (3.6 g; 0.01 mol) was added with stirring, heating being continued at reflux for 5 hours, after which the mixture was cooled and allowed to stand overnight at room temperature. The resultant fine suspension was filtered, and the collected solid was washed with xylene (2×50 ml), tetrachloroethylene (2×50 ml) and dried in vacuo at 50° for 1 hour to afford an off-white solid (38 g). The solid was added to water (100 ml), the solution was basified to pH 10 with aqueous 2 N sodium hydroxide solution, heated on a steam bath for ½ hour and then filtered. The filtrate after cooling to room temperature was acidified to pH 4 by the addition of conc. hydrochloric acid. The resultant precipitate was collected, washed with water, and dried in vacuo to afford an off-white solid 13.86 g; 47% yield).

EXAMPLE 6

The procedure of Example 1 was repeated using toluene (100 ml) as solvent in place of xylene, the reaction mixture being heated at reflux (110°) for 13½ hours. The yield of crude product was 19.45 g (65% yield). Recrystallisation of 19.0 g of the crude product gave 15.22 g (52% overall yield).

EXAMPLE 7

The procedure of Example 3 was repeated but the potassium hydroxide was added as a solid (pellets) followed by a small amount of water (1 ml). After ¾ hour all the water had been removed (11 ml) the reflux temperature reaching 136°. Heating was continued for a further 2¾ hours. The yield of crude product was 46.0 g (77% yield). Recrystallisation of 35.0 g of the crude product gave 28.4 g (63% overall yield).

EXAMPLE 8

The procedure of Example 7 was repeated on half the scale using ortho-xylene (50 ml) as the solvent. After 2 hours all the water had been removed (5.4 ml), the reflux temperature reaching 144°. Heating was then continued for a further 3 hours. The yield of crude product was 20.7 g (70% yield). Recrystallisation of 20.0 g of the crude product gave 17.8 g (62% overall yield).

EXAMPLE 9

The procedure of Example 7 was repeated on half the scale using meta-xylene (50 ml) as the solvent. After 1½ hours all the water had been removed (5.4 ml), the reflux temperature reaching 138°. Heating was then continued for a further 3½ hours. The yield of crude product was 19.8 g (67% yield). Recrystallisation of 19.0 g of the crude product gave 17.0 g (60% overall yield).

EXAMPLE 10

The procedure of Example 7 was repeated on half the scale using para-xylene (50 ml) as the solvent. After 1 hour all the water had been removed (5.4 ml) the reflux temperature reaching 136°. Heating was then continued for a further 3¼ hours. The yield of crude product was 22.2 g (75% yield). Recrystallisation of 21.0 g of the crude product gave 17.7 g (63% overall yield).

EXAMPLE 11

The procedure of Example 7 was repeated on half the scale using ethylbenzene (50 ml) as the solvent. After 1 hour all the water had been removed (5.2 ml) the reflux temperature reaching 135°. Heating was then continued for a further 3¼ hours. The yield of crude product was 21.3 g (72% yield). Recrystallisation of 20.0 g of the crude product gave 17.2 g (62% overall yield).

The process of the invention is an example of the application of the Ullman reaction but avoids the use of the polar solvent nitrobenzene. Nitrobenzene is a solvent which is often difficult to remove from a product and which is now recognised as being highly toxic, the maximum permissible concentration in the atmosphere being 1 ppm.

In a comparative example the reaction conditions essentially of Example 2 (∼ same temperature) were repeated using nitrobenzene as solvent.

COMPARATIVE EXAMPLE

Potassium hydroxide (12.44 g; 85.4% pure; 0.19 mol) in water (10 ml) was added to 2-chlorophenylacetic acid (17.05 g; 0.1 mol) and 2,4-dichlorophenol (16.3 g; 0.1 mol) in nitrobenzene (100 ml), with additional water (5 ml) being used to wash in any remaining potassium hydroxide solution. The mixture was heated with stirring under nitrogen (bath temperature 140°) and the azeotroped water collected using a Dean and Stark apparatus. After 4 hours water (17 ml) and nitrobenzene (2½ ml) had been removed. Heating was discontinued, additional nitrobenzene (2½ ml) was added and the mixture was sealed and allowed to stand overnight at room temperature.

The mixture was reheated to 120° under nitrogen to melt the solids. Cuprous chloride (0.2 g; 0.002 mol) was added with stirring and the mixture heated to 138°. Heating was discontinued after 3½ hours when the mixture was allowed to cool to below 100°. Water (75 ml) was added and the mixture stirred. The aqueous layer was separated, the nitrobenzene layer was extracted with water (75 ml) and the combined aqueous extracts washed with tetrachloroethylene (2×10 ml).

The aqueous extracts were acidified to pH 4 by the addition of conc. hydrochloric acid. The precipitated product, an oil which solidified on scratching, was collected, washed with water and dried in vacuo (60°) to afford 2-(2,4-dichlorophenoxy)phenylacetic acid as a pale brown solid (16.5 g; 56% yield). A portion of the solid (15 g) was recrystallized from tetrachloroethylene (15 ml), the product being collected, washed with tetrachloroethylene (2×5 ml) and dried in vacuo (60°) to afford pure product (13.3 g; 49% overall yield).

That 2-(2,4-dichlorophenoxy)phenylacetic acid can be successfully prepared by the process of the invention is surprising in view of the fact (as described below) the similar reaction when applied to the preparation of 4-(2,4-dichlorophenoxy)phenylacetic acid failed to afford any of the desired material.

ATTEMPTED PREPARATION OF 4-(2,4-dichlorophenoxy)phenylacetic acid

A mixture of potassium hydroxide (12.44 g; 85.4% pure; 0.19 mol), water (15 ml), 4-chlorophenylacetic acid (17.05 g; 0.1 mol) and 2,4-dichlorophenol (16.3 g; 0.1 mol) in xylene (100 ml) was stirred under nitrogen for ½ hour. The mixture was heated to remove the water azeotropically using a Dean & Stark which had been pre-filled with xylene to ensure that no loss of solvent occured. After 1¼ hours 19 ml of water had been removed and the reflux temperature was 135°. Cuprous chloride (0.2 g; 0.002 mol) was added and heating at reflux was continued for a further 3½ hours after which the mixture was cooled and allowed to stand overnight at room temperature. A sample when examined by h.p.l.c. failed to show the presence of any 4-(2,4-dichlorophenoxy)phenylacetic acid. Water (50 ml) was added and the mixture stirred.

The resultant suspension was filtered and the solid washed with water (50 ml), then xylene (20 ml) and dried in vacuo to afford a yellow solid (3.052 g). The bulk of this solid (2.5 g) was recrystallised from tetrachloroethylene (30 ml) to give white crystals (2.005 g; 80% recovery) m.p. 207°–208° of 2,7-dichlorodibenzodioxan (yield of the pure dioxin 19%).

The aqueous and xylene layers of the original filtrate were separated. The xylene layer was extracted with water (50 ml), the combined aqueous layers were washed with tetrachloroethylene (10 ml) and acidified to pH 5.73 with conc. hydrochloric acid when a white solid and a pale brown oil precipitated. The mixture was filtered, the solid washed with water (20 ml), then petroleum ether (b.p. <40°) and dried in vacuo to afford a white solid (2.03 g) shown by h.p.l.c. to be 4-chlorophenylacetic acid. The filtrate consisted of an aqueous layer over a brown oil which in due course crystallised. The aqueous layer was decanted and the crystallised oil was washed with water, dissolved in diethyl ether, dried ($Na_2SO_4$), evaporated to afford an oil which crystallised to a solid, which was triturated with petroleum ether (b.p. <40°), filtered, washed with petroleum ether b.p. <40°) and dried to afford a white solid (3.65 g) shown by h.p.l.c. to be 4-chlorophenylacetic acid. The aqueous layer was acidified to pH 0–1 with conc. hydrochloric acid and the resultant solid collected, washed with water and dried in vacuo to afford a white solid (8.85 g) also shown by h.p.l.c. to be 4-chlorophenylacetic acid.

The three crops of crude 4-chlorophenylacetic acid (14.53 g; 85% recovery) were combined, dissolved in 1 N aqueous sodium hydroxide solution (100 ml), treated with decolourising charcoal, filtered, acidified to pH 0–1 with conc. hydrochloric acid and the resultant solid collected, washed with water and dried in vacuo to afford 4-chlorophenylacetic acid as a white solid (13.56 g) m.p. 103°–105° representing an 80% recovery of unreacted starting material.

We claim:

1. A process for the preparation of 2-(2,4-dichlorophenoxy)phenylacetic acid in which equimolar proportions of the potassium salts of 2-chlorophenylacetic acid and 2,4-dichlorophenol are reacted in toluene, xylene, ethylbenzene, cumene or mixtures thereof, at a temperature in the range 100° C. to the boiling point of the reaction mixture, in the presence of a copper chloride catalyst, followed thereafter by acidification.

2. A process as claimed in claim 1 wherein the copper chloride catalyst is cupric chloride, cuprous chloride or cuprous chloride/mono triphenyl phosphine complex.

3. A process as claimed in claim 1 wherein the process is carried out in xylene at reflux with cupric chloride or cuprous chloride catalyst.

4. A process as claimed in claims 1 to 3 wherein the catalyst is used at a molar ratio of 0.02 to 0.10 based on the potassium salts.

* * * * *